US00PP24558P3

(12) United States Plant Patent

Klemm et al.

(10) Patent No.: US PP24,558 P3

(45) Date of Patent: Jun. 17, 2014

(54) *OSTEOSPERMUM* PLANT NAMED 'KLEOE12198'

(50) Latin Name: *Osteospermum ecklonis* Norl.
Varietal Denomination: KLEOE12198

(75) Inventors: Nils Klemm, Stuttgart (DE); Silke Wagener, Leinfelden-Echterdingen (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 39 days.

(21) Appl. No.: 13/573,347

(22) Filed: Sep. 11, 2012

(65) Prior Publication Data

US 2014/0075625 P1 Mar. 13, 2014

(51) Int. Cl.
*A01H 5/00* (2006.01)

(52) U.S. Cl.
USPC ..... Plt./360

(58) Field of Classification Search
USPC ..... Plt./360
See application file for complete search history.

*Primary Examiner* — Kent L Bell

(74) *Attorney, Agent, or Firm* — Jondle Plant Sciences Division of Swanson & Bratschun, L.L.C.

(57) ABSTRACT

A new and distinct *osteospermum* variety named 'KLEOE12198' particularly distinguished by a uniformly enlarged disc floret corolla and an upright, freely branching growth habit, is disclosed.

1 Drawing Sheet

Genus and species: *Osteospermum ecklonis* Norl.
Variety denomination: 'KLEOE12198'.

BACKGROUND OF THE NEW PLANT

The present invention comprises a new and distinct variety of *osteospermum*, botanically known as *Osteospermum ecklonis* Norl., and hereinafter referred to by the variety name 'KLEOE12198'. The new variety originated from a controlled cross conducted in the summer of 2008 in Stuttgart, Germany between female *osteospermum* plant named 'Mutant 1' (unpatented), and male *osteospermum* plant named 'KLEOE05116' (U.S. Plant Pat. No. 18,576). A single plant selection was subsequently chosen for further evaluation and asexual propagation.

The new variety was first propagated via vegetative cuttings in May of 2009 in Stuttgart, Germany and has been asexually reproduced repeatedly by vegetative cuttings for three to four generations. The present invention has been found to retain its distinctive characteristics through successive asexual propagations via vegetative cuttings.

Plant Breeder's Rights for this variety have not been applied for. 'KLEOE12198' has not been made publicly available or sold more than one year prior to the filing date of this application.

SUMMARY OF THE INVENTION

The following are the most outstanding and distinguishing characteristics of the new variety when grown under normal horticultural practices in Stuttgart, Germany.

1. Uniformly enlarged disc floret corolla; and
2. Upright, freely branching growth habit.

DESCRIPTION OF THE PHOTOGRAPH

This new *osteospermum* plant is illustrated by the accompanying photograph which shows overall plant habit including blooms, buds, and foliage of the plant in full color. The colors shown are as true as can be reasonably obtained by conventional photographic procedures. The photograph was taken in the spring of 2012 on a 3-month old plant grown in a field in Stuttgart, Germany, under conditions which approximate those generally used in normal horticultural practice.

DESCRIPTION OF THE NEW VARIETY

The following detailed descriptions set forth the distinctive characteristics of 'KLEOE12198'. The data which define these characteristics were collected from asexual reproductions carried out in Stuttgart, Germany. The plant history was taken in the spring of 2012 on 7-month old plants grown in 12 centimeter pots planted into the ground at week 20. The plants were grown in a field and pinched at week 6. Color readings were taken under natural light. Color references are primarily to The R.H.S. Colour Chart of The Royal Horticultural Society of London (R.H.S.), Fifth Edition (2007).

DETAILED BOTANICAL DESCRIPTION OF THE NEW PLANT

Classification:
- *Family*.—Asteraceae.
- *Botanical name*.—*Osteospermum ecklonis* Norl.
- *Common name*.—African daisy.
- *Denomination*.—'KLEOE12198'.

Parentage:
- *Female parent*.—*Osteospermum* plant named 'Mutant 1' (unpatented).
- *Male parent*.—*Osteospermum* plant named 'KLEOE05116' (U.S. Plant Pat. No. 18,576).

Plant:
- *Form and habit*.—Herbaceous perennial, usually cultivated as an annual.
- *Growth habit*.—Upright.
- *Branching habit*.—Freely branching.

*Height* (*from top of soil*).—27.0 cm.
*Width* (*including inflorescence*).—36.0 cm.
*Propagation*.—Vegetative cuttings from tips.
*Time to produce a finished flowering plant*.—14 to 16 weeks.
*Time to initiate and develop roots*.—3 to 4 weeks.
*Root description*.—Freely rooting.

Leaves:
*Arrangement*.—Arranged in a whorl.
*Shape*.—Dentiform.
*Apex*.—Obtuse.
*Base*.—Acute.
*Margin*.—Serrate.
*Color*.—Immature leaves: Upper surface: RHS 137B. Lower surface: RHS 137C. Mature leaves: Upper surface: RHS 137A. Lower surface: RHS 146B.
*Length*.—5.0 cm.
*Width*.—2.5 cm.
*Texture*.—Leathery.
*Petiole*.—Absent.

Stems:
*Total number of branches*.—5 to 7.
*Length*.—18.0 cm.
*Diameter*.—0.6 cm.
*Internode length*.—1.0 cm.
*Color*.—RHS 144A.
*Texture*.—Smooth.

Inflorescence buds:
*Shape*.—Obovate.
*Length*.—1.0 cm.
*Diameter*.—0.9 cm.
*Color* (*at tight bud just before the ray florets unfold*).—RHS 143B.

Inflorescence:
*Type*.—Single.
*Blooming habit*.—Spring to autumn.
*Quantity of inflorescences per plant*.—8 to 10.
*Lastingness of the inflorescences on the plant*.—10 to 14 days.
*Fragrance*.—Absent.
*Inflorescence diameter*.—5.0 cm.
*Inflorescence depth*.—1.5 cm to 2.0 cm.
*Disc diameter*.—3.0 cm.

Disc florets:
*Quantity per inflorescence*.—50 to 60.
*Shape*.—Oblanceolate.
*Tube color*.—Closed: RHS N80B. Mature: RHS N78A.
*Length*.—1.4 cm.
*Diameter* (*at apex*).—0.2 cm.
*Apex*.—Obtuse.
*Apex color*.—RHS 79B.
*Base*.—Fused to form a tube.
*Margin*.—Dentate.

Ray florets:
*Quantity per inflorescence*.—22.
*Shape*.—Oblanceolate.
*Color*.—Upper surface: RHS N78A and RHS 77D. Lower surface: RHS 77A.
*Length*.—2.2 cm.
*Width*.—0.7 cm.
*Apex*.—Obovate.
*Base*.—Acute.
*Margin*.—Entire.
*Texture*.—Smooth.

Peduncle:
*Length*.—10.0 cm.
*Diameter*.—0.2 cm.
*Texture*.—Rough.
*Color*.—RHS 143A.

Phyllaries:
*Arrangement*.—Single.
*Observed quantity per inflorescence*.—20.
*Shape*.—Lanceolate.
*Color*.—Upper surface: RHS 138A. Lower surface: RHS 138B.
*Length*.—1.1 cm.
*Width*.—0.1 cm.
*Apex*.—Acute.
*Base*.—Obtuse.
*Margin*.—Entire.
*Texture*.—Rough.

Reproductive organs:
*Androecium*.—Location: Base of the disc floret corolla. Stamens: Quantity: 50 to 60. Shape: Filamentous. Color: RHS N77C. Filament length: 0.3 cm. Filament diameter: 0.02 cm. Anther: Shape: Elliptical. Color: RHS N77A. Length: 0.1 cm. Diameter: 0.02 cm. Pollen: Color: RHS 13A. Amount: Sparse.
*Gynoecium*.—Location: Base of the ray florets; stigmas in disc florets are degenerated and non-functional. Pistils: Number: 22. Length: 0.4 cm. Diameter: 0.02 cm. Stigma: Color: RHS 83A. Shape: Bipartite. Length: 0.1 cm. Diameter: 0.01 cm. Style: Color: RHS 83D. Length: 0.2 cm. Diameter: 0.01 cm. Shape: Filamentous.

Fruit and seed set: Seed set observed.

Disease and insect/pest resistance: No specific observations were made.

COMPARISON WITH PARENTAL AND COMMERCIAL VARIETIES

'KLEOE12198' differs from the female parent *osteospermum* plant 'Mutant 1' (unpatented) in that 'KLEOE12198' has a uniformly enlarged disc floret corolla and purple flowers, whereas 'Mutant 1' has a partially enlarged disc floret corolla and pink-purple flowers.

'KLEOE12198' differs from the male parent *osteospermum* plant 'KLEOE05116' (U.S. Plant Pat. No. 18,576) in that 'KLEOE12198' has dentiform shaped leaves with an obtuse apex and serrate margin, whereas 'KLEOE05116' has obovate shaped leaves with an acute apex and crenate margin. Additionally, 'KLEOE12198' has a uniformly enlarged disc floret corolla, whereas 'KLEOE05116' has a normal sized disc floret corolla.

'KLEOE12198' differs from commercial variety 'KLEOE10180' (U.S. Plant Pat. No. 23,304) in that 'KLEOE12198' has purple disc florets, whereas 'KLEOE10180' has pink disc florets.

We claim:

1. A new and distinct variety of *osteospermum* plant named 'KLEOE12198' as shown and described herein.

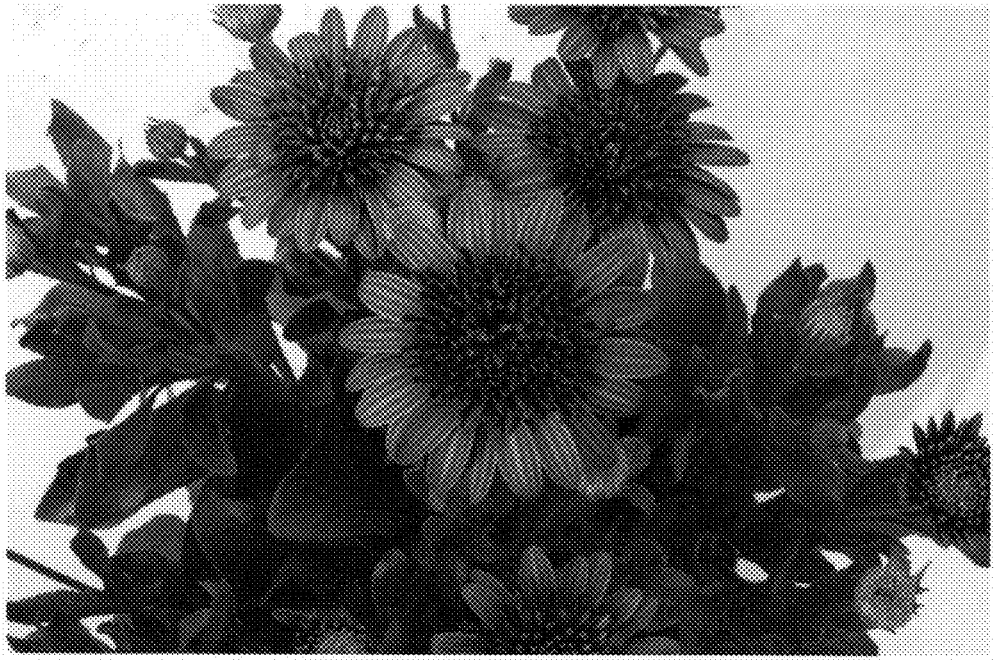

* * * * *